United States Patent
Takita et al.

(10) Patent No.: US 10,861,898 B2
(45) Date of Patent: Dec. 8, 2020

(54) IMAGING DEVICE AND X-RAY IMAGING DEVICE

(71) Applicant: Sharp Kabushiki Kaisha, Osaka (JP)

(72) Inventors: Rikiya Takita, Sakai (JP); Wataru Nakamura, Sakai (JP); Fumiki Nakano, Sakai (JP); Kazuhide Tomiyasu, Sakai (JP); Makoto Nakazawa, Sakai (JP); Hiroyuki Moriwaki, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 16/493,365

(22) PCT Filed: Mar. 15, 2018

(86) PCT No.: PCT/JP2018/010251
§ 371 (c)(1),
(2) Date: Sep. 12, 2019

(87) PCT Pub. No.: WO2018/169009
PCT Pub. Date: Sep. 20, 2018

(65) Prior Publication Data
US 2020/0035745 A1     Jan. 30, 2020

(30) Foreign Application Priority Data
Mar. 16, 2017   (JP) .................. 2017-051166

(51) Int. Cl.
*H01L 27/146*     (2006.01)
*H01L 29/786*     (2006.01)
(Continued)

(52) U.S. Cl.
CPC ...... *H01L 27/14663* (2013.01); *A61B 6/4233* (2013.01); *G01T 1/2018* (2013.01); *H01L 29/7869* (2013.01); *G01T 1/2023* (2013.01)

(58) Field of Classification Search
CPC ............ H01L 27/144; H01L 27/14663; H01L 27/14614; H01L 29/78693; G01T 1/2018; G01T 1/2023
See application file for complete search history.

(56) References Cited

U.S. PATENT DOCUMENTS

| | | |
|---|---|---|
| 2002/0139980 A1 | 10/2002 | Yamazaki |
| 2011/0019042 A1 | 1/2011 | Yamaguchi |

(Continued)

FOREIGN PATENT DOCUMENTS

| | | |
|---|---|---|
| JP | 2000-223716 A | 8/2000 |
| JP | 2011-029337 A | 2/2011 |

(Continued)

OTHER PUBLICATIONS

Official Communication issued in International Patent Application No. PCT/JP2018/010251, dated Jun. 5, 2018.

*Primary Examiner* — Don K Wong
(74) *Attorney, Agent, or Firm* — Keating & Bennett, LLP (57) ABSTRACT

An imaging device according to an embodiment of the present invention includes a photoelectric conversion part that converts incident light into electric charge, and a detection part that detects the electric charge generated in the photoelectric conversion part. The photoelectric conversion part includes a plurality of photodiodes arranged in a matrix, and the detection part includes a plurality of thin film transistors provided corresponding to the plurality of photodiodes and arranged in a matrix. Each of the photodiodes includes a lower electrode, a semiconductor layer, and an upper electrode, and an insulating layer is provided between at least a portion of the lower electrode in the thickness (Continued)

direction and the semiconductor layer in the peripheral portion of the semiconductor layer. An end of the insulating layer has a tapered shape having an acute angle between the lower surface and the side surface of the insulating layer.

7 Claims, 5 Drawing Sheets

(51) Int. Cl.
    *G01T 1/20*     (2006.01)
    *A61B 6/00*     (2006.01)
    *G01T 1/202*     (2006.01)

(56) References Cited

U.S. PATENT DOCUMENTS

| | | |
|---|---|---|
| 2014/0091203 A1 | 4/2014 | Fujiyoshi et al. |
| 2015/0102449 A1 | 4/2015 | Kudo |
| 2017/0148834 A1 | 5/2017 | Tomyo |
| 2020/0091222 A1* | 3/2020 | Nakazawa ............ G01T 1/2018 |

FOREIGN PATENT DOCUMENTS

| | | |
|---|---|---|
| JP | 2014-075377 A | 4/2014 |
| JP | 2015-079840 A | 4/2015 |
| WO | 2015/186657 A1 | 12/2015 |

* cited by examiner

IMAGING DEVICE AND X-RAY IMAGING DEVICE

TECHNICAL FIELD

Some aspects of the present invention relate to an imaging device and an X-ray imaging device.

This application claims priority to Japanese Patent Application No. 2017-051166 filed on Mar. 16, 2017, the contents of which are incorporated herein.

BACKGROUND ART

An X-ray imaging device has been known in, for example, the medical diagnostic device field. There are two systems for X-ray imaging devices: a direct conversion system and an indirect conversion system. In the indirect conversion system of the two systems, an X-ray imaging device convers the irradiated X-rays into visible light by an X-ray conversion layer and detects the visible light as an image by using photodiodes and switching elements.

Patent Literature 1 discloses a photoelectric conversion device including a plurality of photodetecting elements arranged in a matrix. The photodetecting elements each include a photodiode and a thin film transistor. In the specification of the present invention, the thin film transistor is abbreviated as "TFT" hereinafter.

CITATION LIST

Patent Literature

PTL 1: Japanese Unexamined Patent Application Publication No. 2015-79840

SUMMARY OF INVENTION

Technical Problem

The photoelectric conversion device of Patent Literature 1 includes an insulating layer, which has an opening and is provided on a lower electrode of the photodiode for the purpose of suppressing a leakage current of the photodiode, and uses a configuration in which a semiconductor layer (contact layer) of the photodiode is brought into contact with the lower electrode in the opening. However, this configuration has insufficient measures against a leakage current, and a measure to further decrease the leakage current of the photodiode is required.

An aspect of the present invention has been achieved for solving the problem described above, and an object thereof is to provide an imaging device having excellent imaging performance due to a decrease in leakage current of a photodiode. Another object according to an aspect of the present invention is to provide an X-ray imaging device including the imaging device.

Solution to Problem

In order to achieve the objects described above, an imaging device according to an aspect of the present invention includes a photoelectric conversion part which converts incident light into electric charge, and a detection part which detects the electric charge generated in the photoelectric conversion part. The photoelectric conversion part includes a plurality of photodiodes arranged in a matrix, and the detection part includes a plurality of thin film transistors provided corresponding to the plurality of photodiodes and arranged in a matrix. Each of the photodiodes includes a lower electrode, a semiconductor layer, and an upper electrode, and an insulating layer is provided between at least a portion of the lower electrode in the thickness direction and the semiconductor layer in the peripheral portion of the semiconductor layer. An end of the insulating layer has a tapered shape which has an acute angle between the lower surface and the side surface of the insulating layer.

In the imaging device according to the aspect of the present invention, the taper angle θ between the lower surface and the side surface of the insulating layer may satisfy $0 \leq 30°$.

In the imaging device according to the aspect of the present invention, the insulating layer may be a silicon oxide layer.

In the imaging device according to the aspect of the present invention, the insulating layer may have a two-layer structure including a silicon nitride layer and a silicon oxide layer, and the silicon nitride layer may be provided between the lower electrode and the silicon oxide layer.

In the imaging device according to the aspect of the present invention, the lower electrode may have a two-layer structure including a first electrode layer and a second electrode layer, an insulating layer may be provided between the first electrode layer and the second electrode layer in the peripheral portion of the semiconductor layer, and the lower surface of the semiconductor layer may be in contact with the second electrode layer.

In the imaging device according to the aspect of the present invention, the thin film transistors may each include a semiconductor layer composed of an In—Ga—Zn—O— based oxide semiconductor.

An X-ray imaging device according to an aspect of the present invention includes an X-ray conversion part which when irradiated with X-rays, generates light corresponding to the intensity of the X-rays, and the imaging device according to the aspect of the present invention, the photoelectric conversion part converting the light emitted from the X-ray conversion part into the electric charge.

Advantageous Effects of Invention

According to an aspect of the present invention, it is possible to provide an imaging device capable of decreasing a leakage current of a photodiode and thus having excellent imaging performance. According to an aspect of the present invention, it is also possible to provide an X-ray imaging device having excellent imaging performance.

DESCRIPTION OF EMBODIMENTS

First Embodiment

A first embodiment of the present invention is described below by using FIG. 1 to FIG. 4.

An X-ray imaging device of this embodiment is an example of an X-ray imaging device using an indirect conversion system.

Figure 1:
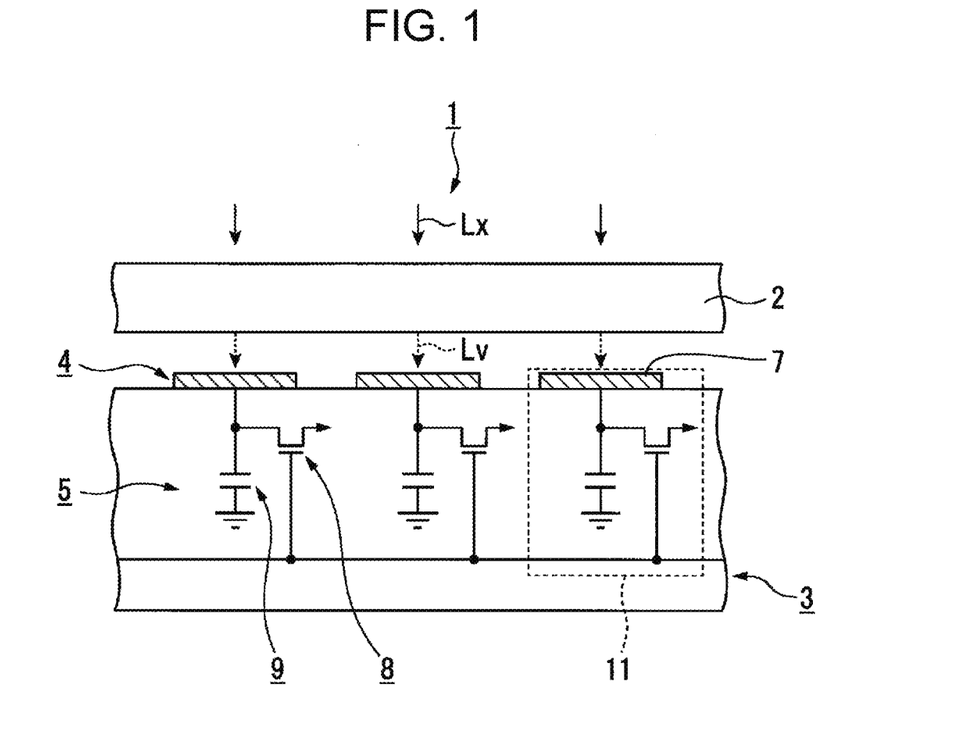
FIG. 1 is a schematic configuration diagram of an X-ray imaging device according to a first embodiment.

FIG. 1 is a schematic configurational diagram of an X-ray imaging device of this embodiment.

In the drawings below, constituent components may be shown at different dimensional scales in order to make the constituent components easy to see.

As shown in FIG. 1, an X-ray imaging device 1 includes an X-ray conversion part 2 and an imaging device 3. The X-ray conversion part 2 generates visible light Lv according to the intensity of X-rays Lx when irradiated with X-rays Lx. The X-ray conversion part 2 is composed of, for example, a known scintillator such as CsI:Tl, $Gd_2O_2S$:Tb, or the like. The imaging device 3 images an image based on the visible light Lv generated by the X-ray conversion part 2.

The imaging device 3 includes a photoelectric conversion part 4 and a detection part 5. The photoelectric conversion part 4 includes a plurality of photodiodes 7 arranged in a matrix. The detailed configuration of the photodiodes 7 is described later. The photoelectric conversion part 4 convers the incident visible light Lv into electric charge.

The detection part 5 includes a plurality of TFTs 8 and a plurality of capacitors 9 arranged in a matrix. The detection part 5 detects the electric charge generated by the photoelectric conversion part 4. The plurality of TFTs 8 are provided corresponding to the plurality of respective photodiodes 7 of the photoelectric conversion part 4 and are electrically connected to the respective photodiodes 7. In addition, the plurality of capacitors 9 are provided corresponding to the plurality of respective TFTs 8 and are electrically connected to the respective TFTs 8. The capacitors 9 temporarily store the electric charge generated by the photoelectric conversion part 4. The TFTs 8 read the electric charge temporarily stored in the capacitors 9.

The photodiodes 7, the TFTs 8, and the capacitors 9 constitute respective pixels 11 of the imaging device 3. The imaging device 3 images an image by reading, in each of the pixels 11, the electric charge generated corresponding to the intensity of the visible light Lv incident from the X-ray conversion part 2.

Figure 2:
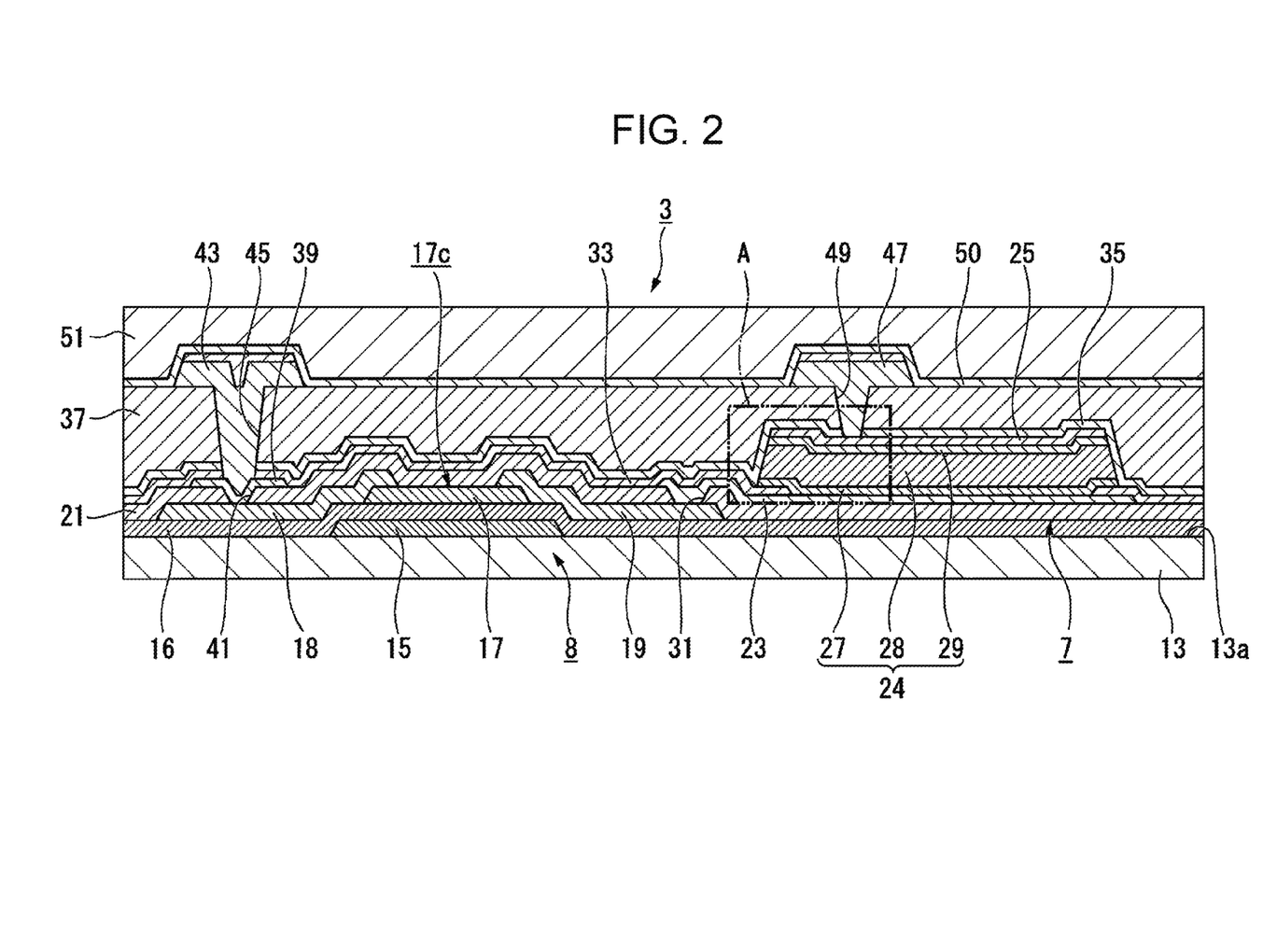
FIG. 2 is a sectional view of an imaging device according to the first embodiment.

FIG. 2 is a sectional view of the imaging device 3 according to this embodiment.

As shown in FIG. 2, the TFTs 8 and the photodiodes 7 are provided on a first surface 13a of a substrate 13. Each of the TFTs 8 includes a gate electrode 15, a gate insulating film 16, an oxide semiconductor layer 17, a source electrode 18, and a drain electrode 19. In this embodiment, each of the TFTs 8 is composed of a channel etch-type bottom gate TFT.

The gate electrode 15 is formed on the first surface 13a of the substrate 13. The gate electrode 15 is composed of, for example, a laminated film of W (tungsten)/Ta (tantalum). The gate insulating film 16 is formed on the first surface 13a of the substrate 13 so as to cover the gate electrode 15. The gate insulating film 16 is composed of, for example, a laminated film of $SiO_2$ (silicon oxide layer)/$SiN_x$ (silicon nitride layer).

The oxide semiconductor layer 17 is formed on the gate insulating film 16. The oxide semiconductor layer 17 is composed of, for example, an In—Ga—Zn—O-based oxide semiconductor. An etch stop layer is not formed on a channel region 17c of the oxide semiconductor layer 17, and the lower surfaces at the channel region 17c-side ends of the source electrode 18 and the drain electrode 19 are disposed to be in contact with the upper surface of the oxide semiconductor layer 17. Each of the source electrode 18 and the drain electrode 19 is composed of, for example, a three-layer laminated metal film of Ti (titanium)/Al (aluminum)/Ti (titanium). Each of the channel etch-type TFTs 8 is formed by, for example, forming a conductive film for a source-drain electrode on the oxide semiconductor layer 17 and then performing source-drain separation. In the source-drain separation step, the surface portion of the channel region 17c may be etched.

The oxide semiconductor contained in the oxide semiconductor layer 17 may be an amorphous oxide semiconductor or a crystalline oxide semiconductor having a crystalline portion. Examples of the crystalline oxide semiconductor include a polycrystalline oxide semiconductor, a microcrystalline oxide semiconductor, a crystalline oxide semiconductor with the c axis oriented substantially perpendicularly to the layer surface, and the like.

The oxide semiconductor layer 17 may have a laminated structure having two or more layers. When the oxide semiconductor layer 17 has a laminated structure, the oxide semiconductor layer 17 may include an amorphous oxide semiconductor layer and a crystalline oxide semiconductor layer. Alternatively, the oxide semiconductor layer 17 may include a plurality of crystalline oxide semiconductor layers having different crystal structures. Also, the oxide semiconductor layer 17 may include a plurality of amorphous oxide semiconductor layers. When the oxide semiconductor layer 17 has a two-layer structure containing an upper layer and a lower layer, the energy gap of the oxide semiconductor contained in the upper layer is preferably larger than the energy gap of the oxide semiconductor contained in the lower layer. However, with a relatively small difference between the energy gaps of these layers, the energy gap of the oxide semiconductor in the lower layer may be larger than the energy gap of the oxide semiconductor in the upper layer.

The materials, structures, film forming methods of the amorphous oxide semiconductor and crystalline oxide semiconductor described above, and the configuration of the oxide semiconductor layer having a laminated structure, etc. are described, for example, in Japanese Unexamined Patent Application Publication No. 2014-007399. For reference, the entire contents disclosed in Japanese Unexamined Patent Application Publication No. 2014-007399 are incorporated in the specification of the present invention.

The oxide semiconductor layer 17 may contain, for example, at least one metal element of In, Ga, and Zn. In this embodiment, the oxide semiconductor layer 17 contains, for example, an In—Ga—Zn—O-based semiconductor (for example, indium-gallium-zinc oxide). In this case, the In—Ga—Zn—O-based semiconductor is a ternary oxide of In (indium), Ga (gallium), and Zn (zinc), and the ratio (composition ratio) of In, Ga, and Zn is not particularly limited and examples of the ratio include In:Ga:Zn=2:2:1, In:Ga:Zn=1:1:1, In:Ga:Zn=1:1:2, and the like. The oxide semiconductor layer 17 can be formed from an oxide semiconductor film containing an In—Ga—Zn—O-based semiconductor.

The In—Ga—Zn—O-based semiconductor may be amorphous or crystalline. The crystalline In—Ga—Zn—O-based semiconductor is preferably a crystalline In—Ga—Zn—O-based semiconductor with the c axis oriented approximately perpendicularly to the layer surface.

The crystal structure of the crystalline In—Ga—Zn—O-based semiconductor is disclosed in, for example, Japanese Unexamined Patent Application Publication No. 2014-007399 described above, Japanese Unexamined Patent Application Publication No. 2012-134475, Japanese Unexamined Patent Application Publication No. 2014-209727, etc. For reference, the entire contents disclosed in Japanese Unexamined Patent Application Publication No. 2012-134475 and Japanese Unexamined Patent Application Publication No. 2014-209727 are incorporated in the specification of the present invention.

TFT having the In—Ga—Zn—O-based oxide semiconductor layer has high mobility (exceeding 20 times as high as a-Si TFT) and low leakage current (less than 1/100 of a-Si TFT). Therefore, the TFT is preferably used as a drive TFT (for example, TFT contained in a drive circuit provided in the periphery of a display region containing a plurality of pixels on the same substrate as the display region) and a pixel TFT (TFT provided in a pixel). The TFT has high mobility and is thus capable of high-speed reading and is preferred for video application. In addition, noise is decreased due to the small off-leakage current of pixel TFTs (the TFTs 8 of the detection part 5), and thus X-ray detection sensitivity can be improved. Also, a TFT/switching element can be miniaturized, thereby giving advantage for higher definition. Further, the leakage current is decreased, thereby giving advantage for lower power consumption.

The oxide semiconductor layer 17 may contain another oxide semiconductor in place of the In—Ga—Zn—O-based semiconductor. For example, an In—Sn—Zn—O-based semiconductor (for example, $In_2O_3$—$SnO_2$—ZnO; InSn-ZnO) may be contained. The In—Sn—Zn—O-based semiconductor is a ternary oxide of In (indium), Sn (tin), and Zn (zinc). The oxide semiconductor layer 17 may contain an In—Al—Zn—O-based semiconductor, an In—Al—Sn—Zn—O-based semiconductor, a Zn—O-based semiconductor, an In—Zn—O-based semiconductor, a Zn—Ti—O-based semiconductor, a Cd—Ge—O-based semiconductor, a Cd—Pb—O-based semiconductor, CdO (cadmium oxide), a Mg—Zn—O-based semiconductor, an In—Ga—Sn—O-based semiconductor, an In—Ga—O-based semiconductor, a Zr—In—Zn—O-based semiconductor, a Hf—In—Zn—O-based semiconductor, or the like.

A first interlayer insulating layer 21 is formed on the gate insulating film 16 so as to cover the source electrode 18 and the drain electrode 19. The first interlayer insulating layer 21 is composed of, for example, a laminated film of $SiO_2$ (silicon oxide film)/$SiN_x$ (silicon nitride film). The photodiodes 7 are formed on the first interlayer insulating layer 21.

Figure 3:
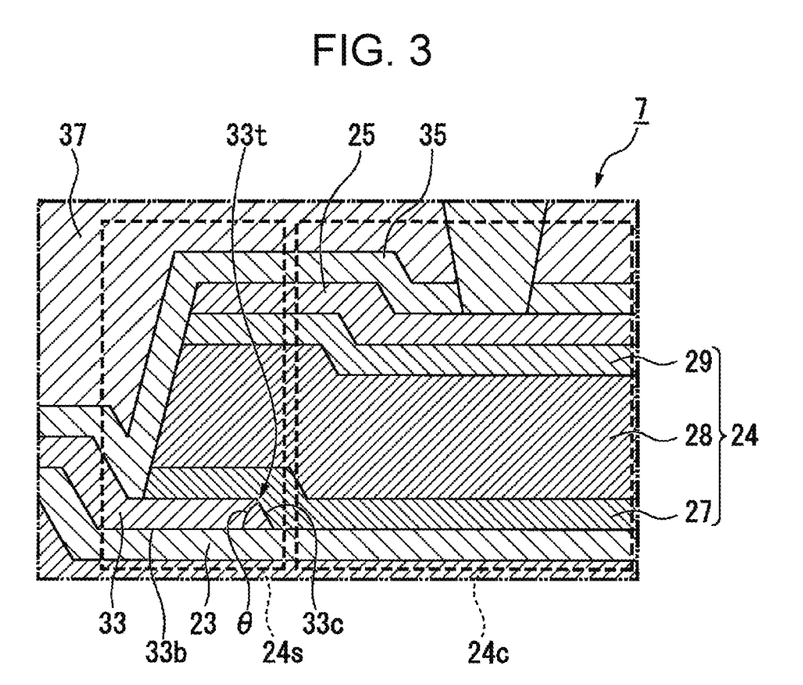
FIG. 3 is an enlarged view of a portion of symbol A in FIG. 2.

FIG. 3 is an enlarged view of a portion (portion of symbol A in FIG. 2) of the photodiodes 7.

As shown in FIG. 3, each of the photodiodes 7 includes a cathode electrode 23 (lower electrode), a semiconductor layer 24, and an anode electrode 25 (upper electrode). The semiconductor layer 24 contains an $n^+$-type silicon layer 27, an i-type silicon layer 28, and a $p^+$-type silicon layer 29 in order from the lower layer side. That is, these layers are disposed so that the $n^+$-type silicon layer 27 is in contact with the cathode electrode 23 and the $p^+$-type silicon layer 29 is in contact with the anode electrode 25. The cathode electrode 23 is composed of, for example, a three-layer laminated metal film of Ti (titanium)/Al (aluminum)/Ti (titanium). The anode electrode 25 is composed of, for example, a transparent conductive film of ITO (indium tin oxide) or the like.

As shown in FIG. 2, an end of the cathode electrode 23 is extended to above the drain electrode 19 of each of the TFTs 8 and is in contact with the drain electrode 19 through a contact hole 31 passing through the first interlayer insulating layer 21. In this configuration, the cathode electrode 23 of each of the photodiodes 7 and the drain electrode 19 of each of the TFTs 8 are electrically connected to each other.

A second interlayer insulating layer 33 is formed on the first interlayer insulating layer 21 so as to cover a contact portion between the cathode electrode 23 and the drain electrode 19. The second interlayer insulating layer 33 is composed of, for example, $SiO_2$ (silicon oxide layer). In the peripheral portion 24s of the semiconductor layer 24 of each of the photodiodes 7, the end of the second interlayer insulating layer 33 is provided at a position held between the cathode electrode 23 and the $n^+$-type silicon layer 27. That is, in the peripheral portion 24s of the semiconductor layer 24, the second interlayer insulating layer 33 is provided between the cathode electrode 23 and the $n^+$-type silicon layer 27. In the central portion 24c of the semiconductor layer 24, where the second interlayer insulating layer 33 is not provided, the cathode electrode 23 is in direct contact with the $n^+$-type silicon layer 27. The second interlayer insulating layer 33 according to this embodiment corresponds to an insulating layer described in the claims.

As shown in FIG. 3, the end 33t of the second interlayer insulating layer 33 has a tapered shape having an acute angle between the lower surface 33b and the side surface 33c of the second interlayer insulating layer 33. The taper angle θ between the lower surface 33b and the side surface 33c of the second interlayer insulating layer 33 may be 0°<θ<90°, but more preferably satisfies θ≤30°.

A third interlayer insulating layer 35 is formed on the second interlayer insulating layer 33 so as to cover the photodiodes 7. The third interlayer insulating layer 35 is composed of, for example, $SiN_x$ (silicon nitride film).

A first planarization layer 37 is formed on the third interlayer insulating layer 35. The step differences caused by the photodiodes 7 and the TFTs 8 are planarized by the planarization layer 37.

A relay electrode 39 is formed in the same layer as the cathode electrode 23 on the first interlayer insulating layer 21. The relay electrode 39 is in contact with the source electrode 18 through a contact hole 41 passing through the first interlayer insulating layer 21.

A source line 43 is formed on the first planarization layer 37. The source line 43 is in contact with the relay electrode 39 through a contact hole 45 passing through the first planarization layer 37, the third interlayer insulating layer 35, and the second interlayer insulating layer 33. According to this configuration, the source line 43 is electrically connected to the source electrode 18 through the relay electrode 39. The source line 43 is composed of, for example, a laminated film of Ti (titanium)/Al (aluminum)/Ti (titanium) and an ITO film.

A bias line 47 is formed in the same layer as the source line 43 on the first planarization layer 37. The bias line 47 is in contact with the anode electrode 25 through a contact hole 49 passing through the first planarization layer 37 and the third interlayer insulating layer 35. According to this configuration, the bias line 47 is electrically connected to the anode electrode 25.

A fourth interlayer insulating layer 50 is formed on the first planarization layer 37 so as to cover the source line 43 and the bias line 47. The fourth interlayer insulating layer 50 is composed of, for example, $SiN_x$ (silicon nitride film). A second planarization layer 51 is formed on the fourth interlayer insulating layer 50. The step differences caused by the source line 43 and the bias line 47 are planarized by the second planarization layer 51.

Figure 4:
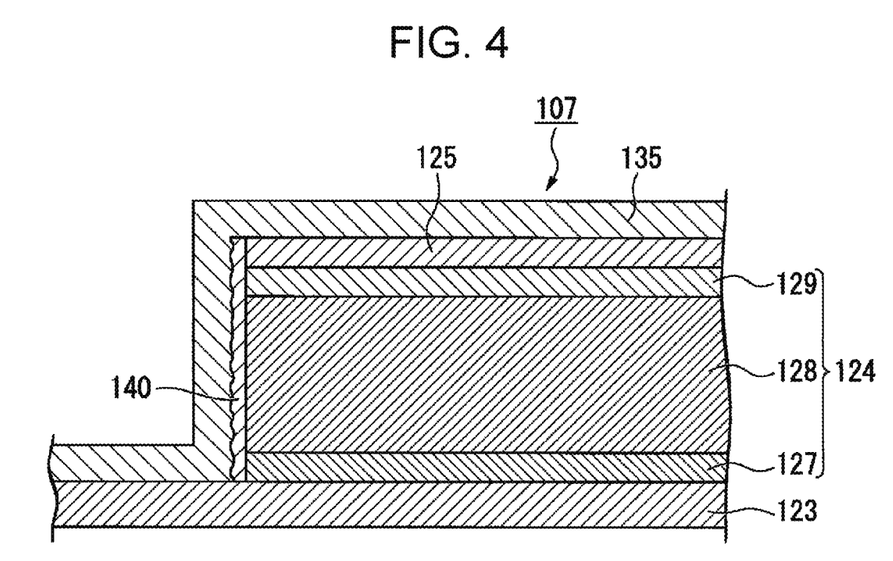
FIG. 4 is a drawing illustrating a problem of an imaging device of a comparative example.

FIG. 4 is a drawing illustrating the problem of an imaging device of a comparative example, which is a sectional view showing only a photodiode portion.

As shown in FIG. 4, in a photodiode 107 in an imaging device of a comparative example, an anode electrode 125 and an $n^+$-type silicon layer 127, an i-type silicon layer 128, and a $p^+$-type silicon layer 129, which constitute a semiconductor layer 124, are patterned so that the end surfaces of these layers are arranged on the same plane. The semiconductor layer 124 and the anode electrode 125 are covered with an insulating film 135. Like in this embodiment, a cathode electrode 123 is extended in the lateral direction to form a contact portion in contact with a drain electrode of TFT.

A process for manufacturing the photodiode 107 includes forming the cathode electrode 123, then laminating a four-layer film constituting the layers of the $n^+$-type silicon layer 127, the i-type silicon layer 128, the $p^+$-type silicon layer 129, and the anode electrode 125 from the lower layer side, and then patterning the four-layer film constituting the layers of the anode electrode 125, the $p^+$-type silicon layer 129, the i-type silicon layer 128, and the $n^+$-type silicon layer 127 by collectively etching the four-layer film.

However, when the four-layer film is collectively etched, the surface of the film serving as the cathode electrode 123 is continuously etched, and thus the etching residue 140 generated from the cathode electrode 123 adheres to the side wall of the four-layer film. Consequently, the etching residue 140 serves as a leakage route and thus easily causes leakage.

In this case, leakage occurs on the diode side surface between the anode electrode 125 and the cathode electrode 123 of the photodiode 107, thereby increasing the dark current level. The photodiode is an important portion playing the function of photoelectric conversion and exhibits the function of taking out electric charge from the upper layer and the lower layer of the photodiode and sending electric signals to an image. Therefore, it is required to secure the characteristics such as the efficiency of photoelectric conversion, uniformity between pixels etc., but the occurrent of the leakage current of the photodiode causes the problems such as a decrease in photodiode sensitivity, deterioration in uniformity, etc., thereby causing the possibility of decreasing the contrast.

On this point, when as in the imaging device 3 of this embodiment, the second interlayer insulating layer 33 is provided between the cathode electrode 23 and the $n^+$-type silicon layer 27 in the peripheral portion of the semiconductor layer 24, the second interlayer insulating layer 33 functions as an etching stopper during collective etching of the four layers of the anode electrode 25, the $p^+$-type silicon layer 29, the i-type silicon layer 28, and the $n^+$-type silicon layer 27.

That is, the surface of the cathode electrode 23 is protected from the etchant by the second interlayer insulating layer 33, and thus the occurrence of etching residue from the cathode electrode 23 is suppressed.

However, as a result of investigation performed by the inventors, it was found that when a second interlayer insulating layer has an end having a shape rising perpendicularly to the substrate surface, a steep step is in the semiconductor layer at a position located at the end of the second interlayer insulating layer, resulting in the possibility of producing small crack in the semiconductor layer and increasing the dark current.

Regarding the problem, in the imaging device 3 of this embodiment, the end 33*t* of the second interlayer insulating layer 33 has a tapered shape having an acute angle between the lower surface 33*b* and the side surface 33*c* of the second interlayer insulating layer 33, and thus the step formed in the semiconductor layer 24 becomes gentle, thereby making it possible to suppress the occurrence of crack. In particular, when the taper angle θ of the second interlayer insulating layer 33 is θ≤30°, the occurrence of crack can be satisfactorily suppressed. This is because when the taper angle θ is larger than 30°, a crack or void easily occurs in the semiconductor layer with the end 33*t* of the second interlayer insulating layer 33 shown in FIG. 3 as a starting point, leading to a defect. As a result, according to this embodiment of the present invention, the X-ray imaging device 1 having a high contrast and excellent imaging performance can be realized.

In addition, this embodiment uses the TFTs 8 each including the In—Ga—Zn—O-based oxide semiconductor layer 17, and thus the off-leakage current of TFT can be decreased as compared with the use of TFT including amorphous silicon (a-Si). With the small off-leakage current of the TFTs 8, the X-ray detection sensitivity can be improved.

Second Embodiment

A second embodiment of the present invention is described below by using FIG. 5, FIG. 6A, and FIG. 6B.

An X-ray imaging device according to this embodiment has the same basic configuration as the first embodiment, but the configuration of a photodiode is different from the first embodiment.

Figure 5:
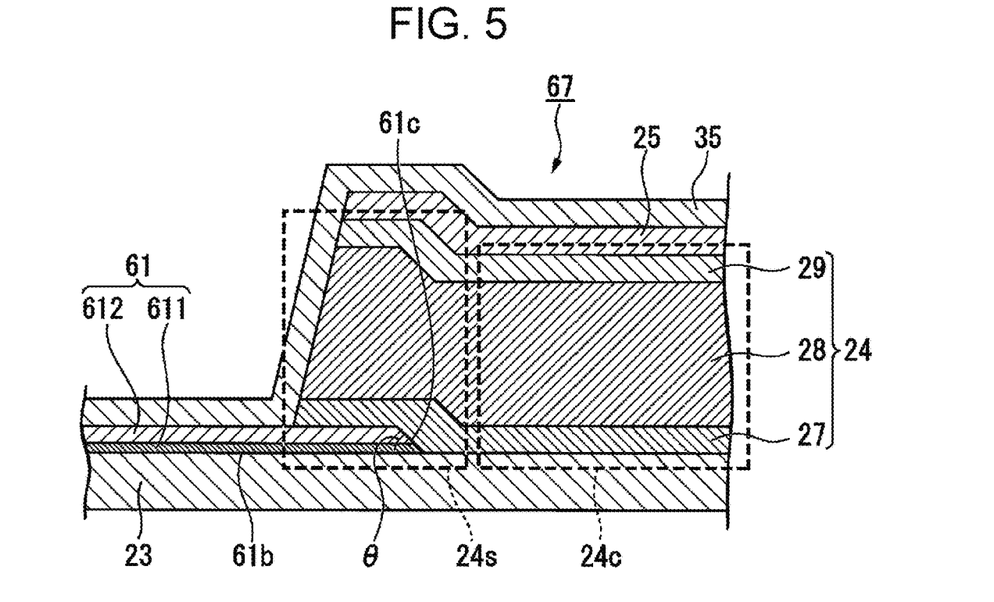
FIG. 5 is a sectional view of an imaging device according to a second embodiment.

FIG. 5 is a sectional view of the imaging device of the second embodiment. FIG. 6A is a drawing illustrating the problem of a process for manufacturing an imaging device. FIG. 6B is a drawing illustrating a method for solving the problem.

Figure 6A:
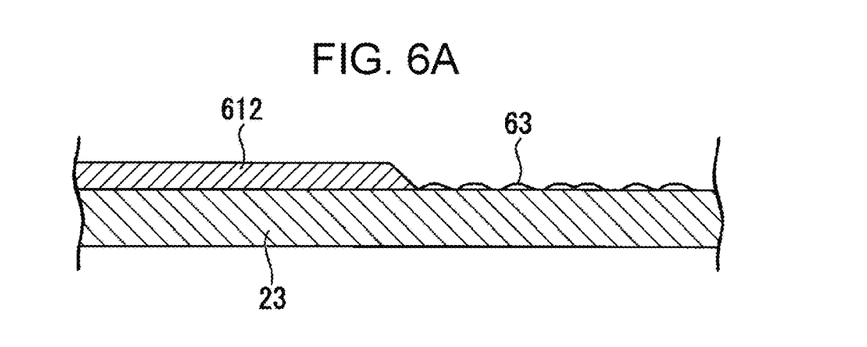
FIG. 6A is a drawing illustrating a problem of a process for manufacturing an imaging device.
Figure 6B:
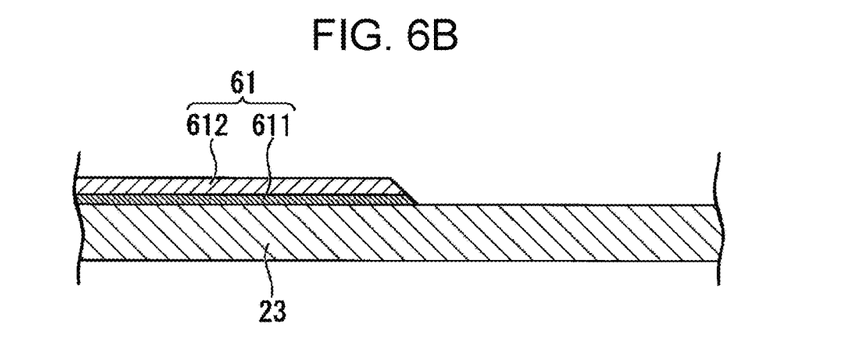
FIG. 6B is a drawing illustrating a method for solving a problem.

In FIG. 5, FIG. 6A, and FIG. 6B, the constituent element common to the drawings used in the first embodiment is denoted by the same reference numeral, and the description thereof is omitted.

As shown in FIG. 5, in the imaging device of this embodiment, an insulating layer 61 is provided between a cathode electrode 23 and a semiconductor layer 24 ($n^+$-type silicon layer 27) in the peripheral portion of the semiconductor layer 24 constituting a photodiode 67. An end of the insulating layer 61 has a tapered shape having an acute angle between the lower surface 61*b* and the side surface 61*c* of the insulating layer 61.

The insulating layer 61 has a two-layer structure including a silicon nitride layer 611 and a silicon oxide layer 612, and the lower layer side is the silicon nitride layer 611 and the upper layer side is the silicon oxide layer 612. That is, the silicon nitride layer 611 is provided between the cathode electrode 23 and the silicon oxide layer 612.

The rest configuration is the same as the first embodiment.

In this embodiment, a crack in the semiconductor layer can be suppressed, and thus the same effect as the first embodiment can be obtained; that is, an X-ray imaging device having high contrast and excellent imaging performance can be realized.

However, as shown in FIG. 6A, in the case of a comparative example in which an insulating layer is composed of only the silicon oxide layer 612, oxidation of the cathode electrode 23 takes place by the oxygen contained in the silicon oxide layer 612, and thus oxide residue 63 may remain on the surface of the cathode electrode 23. In this case, there occurs the problem that ohmic contact cannot be made between the cathode electrode 23 and the n+-type silicon layer 27.

Regarding the problem, according to this embodiment, as shown in FIG. 6B, the insulating layer 61 has a two-layer structure, and the lower layer side of the insulating layer 61 is made of the silicon nitride layer 611, and the upper layer side of the insulating layer 61 is made of the silicon oxide layer 612. Therefore, this embodiment has a structure which decreases a leakage current, and in addition, the occurrence of the oxide residue 63 on the cathode electrode 23 can be suppressed. Therefore, the ohmic contact between the cathode electrode 23 and the n+-type silicon layer 27 can be realized, and thus the photodiode 67 having excellent characteristics can be formed.

Third Embodiment

A third embodiment of the present invention is described below by using FIG. 7.

An X-ray imaging device according to this embodiment has the same basic configuration as the first embodiment, but the configuration of a photodiode is different from the first embodiment.

Figure 7:
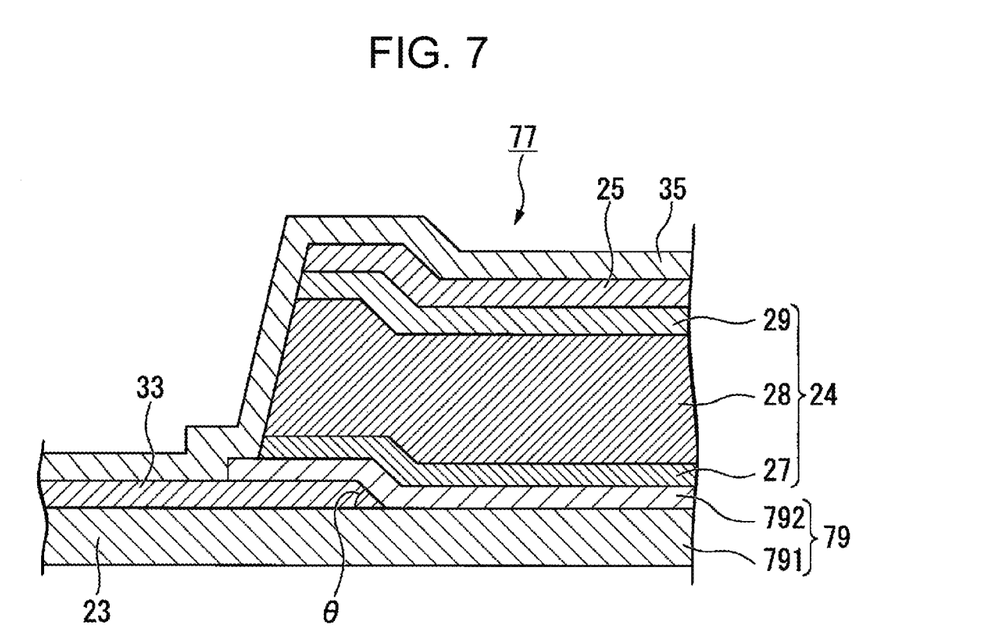
FIG. 7 is a sectional view of an imaging device according to a third embodiment.

FIG. 7 is a sectional view of an imaging device according to a third embodiment.

In FIG. 7, the constituent element common to the drawings used in the first embodiment is denoted by the same reference numeral, and the description thereof is omitted.

As shown in FIG. 7, in an imaging device of this embodiment, a cathode electrode 79 of a photodiode 77 has a two-layer structure including a first electrode layer 791 and a second electrode layer 792. The first electrode layer 791 and the second electrode layer 792 may be composed of the same type of conductive material or may be composed of different types of conductive materials. However, the second electrode layer 792 on the upper layer side is exposed to a washing solution during wet-washing of the end surface of the semiconductor layer 24 and is thus preferably a film type having the resistance to the washing solution.

In the first embodiment, the second interlayer insulating layer 33 is provided between the cathode electrode 23 and the n+-type silicon layer 27 in the peripheral portion 24s of the semiconductor layer 24, while in this embodiment, the second interlayer insulating layer 33 is provided between the first electrode layer 791 and the second electrode layer 792 of the cathode electrode 79 in the peripheral portion 24s of the semiconductor layer 24. That is, the second interlayer insulating layer 33 is disposed between a portion of the cathode electrode 79 in the thickness direction and the semiconductor layer 24 in the peripheral portion 24s of the semiconductor layer 24.

The second electrode layer 792 is provided so that an end of the second electrode layer 792 is extended to the outside of an end of the semiconductor layer 24. Therefore, the entire region of the lower surface of the semiconductor layer 24 is in contact with the second electrode layer 792.

The rest configuration is the same as the first embodiment.

Also, in this embodiment, a crack in the semiconductor layer 24 can be suppressed, and thus the same effect as the first embodiment can be obtained; that is, an X-ray imaging device having high contrast and excellent imaging performance can be realized.

In the configuration of the first embodiment, in the semiconductor layer 24, a portion located above the second interlayer insulating layer 33 is not in direct contact with the cathode electrode 23, and thus a signal delay may occur. With respect to the problem, according to the configuration of this embodiment, the entire region of the semiconductor layer 24 (n+-type silicon layer 27) is in contact with the second electrode layer 792, and thus the occurrence of signal delay can be suppressed.

In addition, the technical scope of the present invention is not limited to the embodiments described above, and various modifications can be added within a range not deviating from the gist of the present invention.

For example, in the embodiments described above, a PIN-type diode is described as an example of photodiodes, but, for example, a PN junction-type diode may be used. In addition, a channel etch-type bottom gate TFT is described as an example of TFT, but, for example, a channel stop-type TFT may be used or a top gate TFT may be used. The other specific description of the number, shape, dimensions, arrangement, materials, etc. of constituent components constituting an imaging device is not limited to the examples described above in the embodiments, and proper modification can be made.

Also, an aspect of the present invention is not limited to an X-ray imaging device and can be applied to an imaging device which images an image by visible light.

INDUSTRIAL APPLICABILITY

Some aspects of the present invention can be used for an imaging device or an X-ray imaging device.

REFERENCE SIGNS LIST

1 X-ray imaging device
2 X-ray conversion part
3 imaging device
4 photoelectric conversion part
5 detection part
7, 67, 77 photodiode
8 TFT (thin film transistor)
17 oxide semiconductor layer
23, 79 cathode electrode (lower electrode)
24 semiconductor layer
25 anode electrode (upper electrode)
33 second interlayer insulating layer (insulating layer)
61 insulating layer
611 silicon nitride layer
612 silicon oxide layer
791 first electrode layer
792 second electrode layer

The invention claimed is:
1. An imaging device comprising:
a photoelectric conversion part that converts incident light into electric charge; and
a detection part that detects the electric charge generated in the photoelectric conversion part,
wherein the photoelectric conversion part includes a plurality of photodiodes arranged in a matrix;
the detection part includes a plurality of thin film transistors provided corresponding to the plurality of photodiodes and arranged in a matrix, each of the photodiodes includes a lower electrode, a semiconductor layer, and an upper electrode;

an insulating layer is provided between at least a portion of the lower electrode in the thickness direction and the semiconductor layer in the peripheral portion of the semiconductor layer; and an end of the insulating layer has a tapered shape having an acute angle between the lower surface and the side surface of the insulating layer.

2. The imaging device according to claim 1, wherein the taper angle θ formed between the lower surface and the side surface of the insulating layer satisfies 0≤30°.

3. The imaging device according to claim 1, wherein the insulating layer is a silicon oxide layer.

4. The imaging device according to claim 1, wherein the insulating layer has a two-layer structure including a silicon nitride layer and a silicon oxide layer; and the silicon nitride layer is provided between the lower electrode and the silicon oxide layer.

5. The imaging device according to claim 1, wherein the lower electrode has a two-layer structure including a first electrode layer and a second electrode layer;

an insulating layer is provided between the first electrode layer and the second electrode layer in the peripheral portion of the semiconductor layer; and the lower surface of the semiconductor layer is in contact with the second electrode layer.

6. The imaging device according to claim 1, wherein each of the thin film transistors includes a semiconductor layer composed of an In—Ga—Zn—O-based oxide semiconductor.

7. An X-ray imaging device comprising:

an X-ray conversion part that generates light corresponding to the intensity of X-rays when irradiated with the X-rays; and the imaging device according to claim 1, wherein the photoelectric conversion part converts light incident from the X-ray conversion part into the electric charge.

\* \* \* \* \*